(12) United States Patent
Rehbein

(10) Patent No.: US 11,338,095 B2
(45) Date of Patent: May 24, 2022

(54) DRUG DELIVERY DEVICE

(71) Applicant: Sanofi-Aventis Deutschland GMBH, Frankfurt am Main (DE)

(72) Inventor: Christian Rehbein, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 574 days.

(21) Appl. No.: 16/317,018

(22) PCT Filed: Jul. 12, 2017

(86) PCT No.: PCT/EP2017/067509
§ 371 (c)(1),
(2) Date: Jan. 10, 2019

(87) PCT Pub. No.: WO2018/011255
PCT Pub. Date: Jan. 18, 2018

(65) Prior Publication Data
US 2019/0224422 A1    Jul. 25, 2019

(30) Foreign Application Priority Data
Jul. 14, 2016 (EP) .................................... 16179491

(51) Int. Cl.
*A61M 5/32* (2006.01)
*A61M 5/20* (2006.01)
(Continued)

(52) U.S. Cl.
CPC ........ *A61M 5/3234* (2013.01); *A61M 5/2053* (2013.01); *A61M 5/2422* (2013.01);
(Continued)

(58) Field of Classification Search
CPC .. A61M 5/2053; A61M 5/2046; A61M 5/155; A61M 2205/8218;
(Continued)

(56) References Cited

U.S. PATENT DOCUMENTS

| 4,031,889 A | 6/1977 | Pike |
| 2005/0015055 A1 | 1/2005 | Yang |

(Continued)

FOREIGN PATENT DOCUMENTS

| CN | 101903058 | 3/2013 |
| CN | 103249443 | 10/2015 |

(Continued)

OTHER PUBLICATIONS

International Preliminary Report on Patentability in International Appln. No. PCT/EP2017/067509, dated Jan. 15, 2019, 7 pages.
(Continued)

*Primary Examiner* — Kevin C Sirmons
*Assistant Examiner* — Leah J Swanson
(74) *Attorney, Agent, or Firm* — Fish & Richardson P.C.

(57) ABSTRACT

The disclosure relates to a drug delivery device, comprising:
a housing to receive a cartridge with a needle and a stopper, wherein the cartridge is movable within the housing so as to cover the needle within the housing or advance the needle beyond the housing,
a gas tank containing a pressurized gas within the housing, the gas tank connectable with a cavity for moving the cartridge, a cavity for moving the stopper and a cavity for moving the cartridge,
a release member fixed to the housing and adapted to restrict movement of the cartridge relative to the housing in a proximal direction,
a membrane between the cavity and the retraction release member adapted to operate the release member if the
(Continued)

membrane is deformed by a pressure within the cavity exceeding a predetermined value allowing movement of the cartridge relative to the housing in the proximal direction.

20 Claims, 9 Drawing Sheets

(51) Int. Cl.
  *A61M 5/24* (2006.01)
  *A61M 5/31* (2006.01)
(52) U.S. Cl.
  CPC ............... *A61M 5/321* (2013.01); *A61M 5/24* (2013.01); *A61M 2005/2411* (2013.01); *A61M 2005/3125* (2013.01); *A61M 2005/3235* (2013.01); *A61M 2005/3238* (2013.01); *A61M 2205/8225* (2013.01)
(58) Field of Classification Search
  CPC .. A61M 2205/8225; A61M 2205/8231; A61M 5/3234; A61M 5/2422; A61M 5/321; A61M 5/24; A61M 2005/2411; A61M 2005/3125; A61M 2005/3235; A61M 2005/3238
  See application file for complete search history.

(56) References Cited

U.S. PATENT DOCUMENTS

| | | | |
|---|---|---|---|
| 2013/0150801 A1 | 6/2013 | Ekman et al. | |
| 2013/0281927 A1* | 10/2013 | Jennings | A61M 5/2053 |
| | | | 604/143 |
| 2016/0361496 A1* | 12/2016 | Guillermo | A61M 5/2033 |

FOREIGN PATENT DOCUMENTS

| | | |
|---|---|---|
| EP | 2364740 | 9/2011 |
| EP | 2399635 | 12/2011 |
| JP | 2007-222661 | 9/2007 |
| JP | 2013-539684 | 10/2013 |
| WO | WO 2003/068290 | 8/2003 |
| WO | WO 2006/024172 | 3/2006 |
| WO | WO 2009/047247 | 4/2009 |
| WO | WO 2012/045831 | 4/2012 |
| WO | WO 2012/045836 | 4/2012 |

OTHER PUBLICATIONS

International Search Report and Written Opinion in International Appln. No. PCT/EP2017/067509, dated Aug. 11, 2017, 10 pages.

* cited by examiner

DRUG DELIVERY DEVICE

CROSS REFERENCE TO RELATED APPLICATIONS

The present application is the national stage entry of International Patent Application No. PCT/EP2017/067509, filed on Jul. 12, 2017, and claims priority to Application No. EP 16179491.2, filed on Jul. 14, 2016, the disclosures of which are incorporated herein by reference.

TECHNICAL FIELD

The present disclosure generally relates to a drug delivery device.

BACKGROUND

Administering an injection is a process which presents a number of risks and challenges for users and healthcare professionals, both mental and physical. Pre-filled syringes containing a selected dosage of a medicament for administering the medicament to a patient are known in the art.

There remains a need for an improved drug delivery device.

SUMMARY

An aspect of the present disclosure relates to an improved drug delivery device.

According to the present disclosure, a drug delivery device comprises:
- a housing adapted to receive a drug cartridge with an injection needle and a stopper, wherein the drug cartridge is axially movable within the housing so as to operatively cover the injection needle within the housing or advance the injection needle beyond a distal end of the housing,
- a gas tank containing a pressurized gas arranged within the housing, the gas tank operatively connectable with an insertion cavity for moving the drug cartridge in a distal direction, a dispense cavity for moving the stopper in the distal direction and a retraction cavity for moving the drug cartridge in a proximal direction,
- a retraction release member fixed to the housing and adapted to restrict movement of the drug cartridge relative to the housing in the proximal direction,
- a flexible membrane between the dispense cavity or the insertion cavity and the retraction release member adapted to operate the retraction release member if the flexible membrane is deformed by a pressure within the dispense cavity or the insertion cavity exceeding a predetermined value allowing movement of the drug cartridge relative to the housing in the proximal direction.

The drug delivery device of the present disclosure allows for an injection cycle with an automatic sequence of operation. The pressurized gas allows for a particularly high dispensing force suitable for injecting high-viscosity drugs. The acceleration and impact on the drug cartridge is smooth so that the risk of damaging the drug cartridge is reduced. As the gas tank is connected to the cavities, the compressed gas will advance the drug cartridge and the stopper within the cartridge. During this movement, the pressure in the dispense cavity and/or insertion cavity will not exceed the predetermined value as the volume of the dispense cavity keeps increasing due to the moving stopper. As the stopper bottoms out in the syringe, further inflow of pressurized gas cannot further increase the volume but the pressure within the dispense cavity so the flexible membrane is deformed and operates the retraction release allowing movement of the drug cartridge relative to the housing in the proximal direction, i.e., retraction of the syringe and needle. The drug delivery device thus provides post-injection needle safety by automatic needle retraction.

In an exemplary embodiment, the drug delivery device furthermore comprises:
- a retraction member slidably arranged within the housing,
- an insertion member slidably arranged within the retraction member and adapted to hold the drug cartridge such that the insertion member and the drug cartridge cannot move relative to each other in an axial direction, wherein the retraction release member is fixed to the housing and adapted to engage the retraction member for restricting movement of the retraction member relative to the housing in the proximal direction.

In an exemplary embodiment, the insertion cavity is defined within the retraction member and operatively connectable to the gas tank by a flow channel, the insertion cavity adapted to move the insertion member in the distal direction when subjected to pressure.

In an exemplary embodiment, the dispense cavity is defined within the insertion member and adapted to be distally limited by the stopper so as to displace the stopper in the distal direction when subjected to pressure, wherein the dispense cavity is separated from the insertion cavity by a flow limiter in the insertion member.

In an exemplary embodiment, the flexible membrane is arranged in the insertion member adapted to disengage the retraction release member from the retraction member if the flexible membrane is deformed by the pressure within the dispense cavity exceeding the predetermined value.

In an exemplary embodiment, the retraction cavity is defined between the housing and the retraction member and adapted to move the retraction member in the proximal direction when subjected to pressure, wherein the retraction cavity is connected with the insertion cavity by a bleed hole.

In an exemplary embodiment, the insertion member is adapted to engage a proximal collar on the drug cartridge.

In an exemplary embodiment, the gas tank is slidable in an axial direction and comprises a distal wall arranged as or comprising a piercable membrane, wherein a flow channel in the form of a needle having a sharp proximal tip is arranged in the retraction member adapted to pierce the distal wall of the gas tank to connect the gas tank with the insertion cavity.

In an exemplary embodiment, the retraction member comprises a transversal wall and a circumferential wall and/or wherein the insertion member comprises a transversal wall and a circumferential wall.

In an exemplary embodiment, the insertion member comprises a seal member for gas-tightly sealing against the circumferential wall of the retraction member.

In an exemplary embodiment, the retraction release member comprises a radially inwardly directed protrusion adapted to be engaged by the flexible membrane.

In an exemplary embodiment, the retraction release member comprises a hook for engaging a recess in the retraction member.

In an exemplary embodiment, the retraction member is sealed against an inner surface of the housing by two axially spaced seal members, the more proximally arranged seal member arranged on the retraction member and the more distally arranged seal member arranged on the housing thus sealing the retraction cavity.

In an exemplary embodiment, an outer diameter of the retraction member is smaller than an inner circumference of the housing.

In an exemplary embodiment, the seal member is arranged on a circumferential rib on the retraction member and/or wherein the seal member is arranged on a circumferential rib within the housing to radially space the retraction member from the housing.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1:
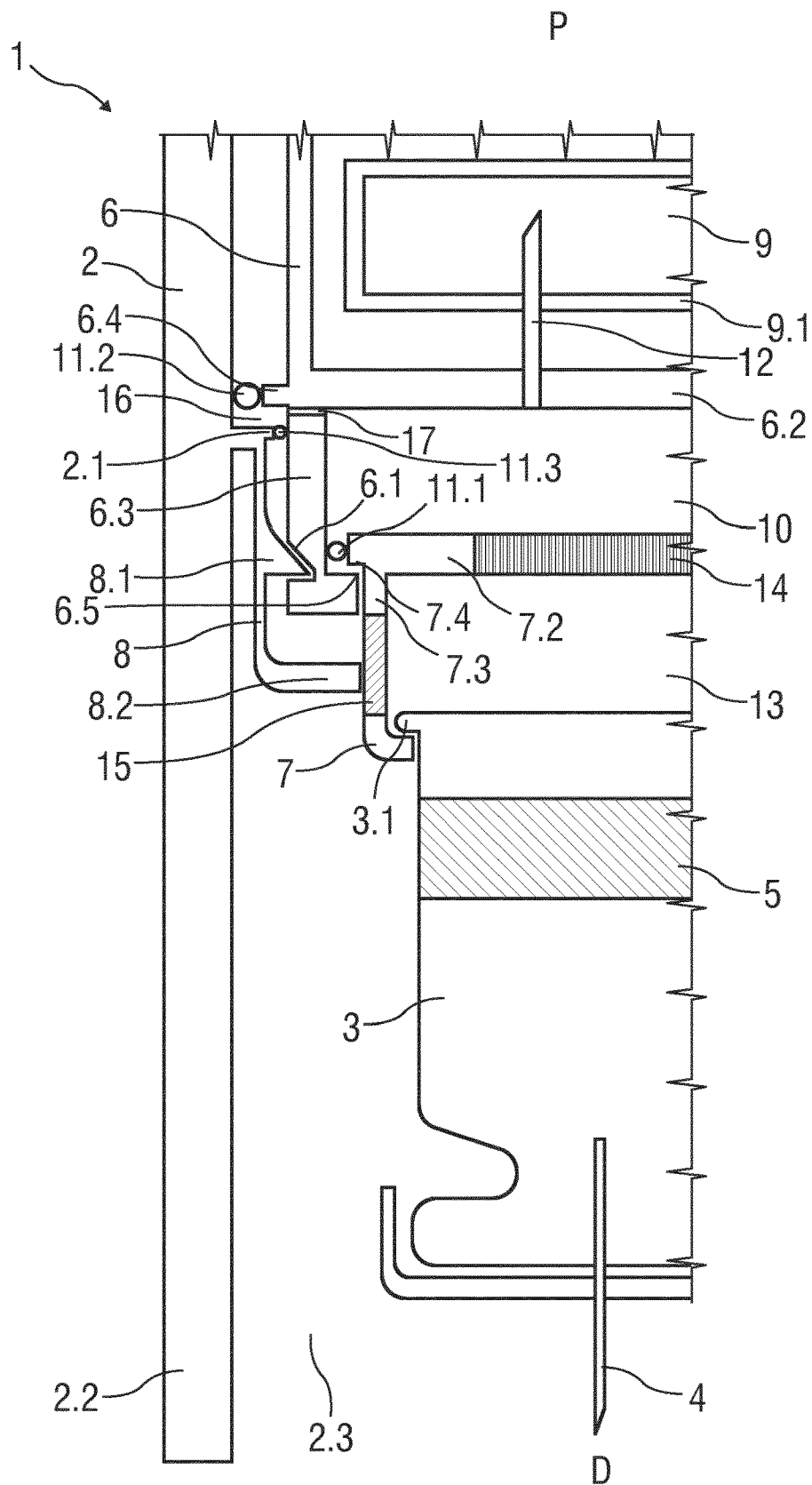
FIG. 1 is a schematic detail view of an exemplary embodiment of a drug delivery device.

FIG. 1 is a schematic detail view of an exemplary embodiment of a drug delivery device 1, comprising a housing 2 adapted to receive a drug cartridge 3. The drug cartridge 3 may have a distal end with a septum to which an injection needle 4 may be attached or the drug cartridge 3 may have the form of a pre-filled syringe with an attached injection needle 4, which may extend from or be extended through an opening 2.3 in a distal end 2.2 of the housing 2. A stopper 5 is arranged within the drug cartridge 3 adapted to seal the drug cartridge 3 proximally and to be moved in a distal direction D to displace a drug contained within the drug cartridge 3 through the injection needle 4. A retraction member 6 is arranged within the housing 2 and slidable in an axial direction relative to the housing 2. The drug cartridge 3 is held by an insertion member 7. In the illustrated embodiment, the insertion member 7 engages a proximal collar 3.1 on the drug cartridge 3 such that the insertion member 7 and the drug cartridge 3 cannot move relative to each other in the axial direction. The insertion member 7 is slidably arranged within the retraction member 6 such that the insertion member 7 and the drug cartridge 3 can move in the axial direction relative to the retraction member 6.

A retraction release member 8 is fixed to the housing 2 and comprises a hook 8.1 for engaging a recess 6.1 in the retraction member 6 thereby restricting movement of the retraction member 6 relative to the housing 2 in a proximal direction P.

A gas tank 9 containing a pressurized gas is arranged within the housing 2 and slidable in an axial direction, the gas tank 9 comprising a distal wall 9.1 arranged as or comprising a piercable membrane.

The retraction member 6 comprises a transversal wall 6.2 and a circumferential wall 6.3. The insertion member 7 also comprises a transversal wall 7.2 and a circumferential wall 7.3. The transversal wall 6.2 and the circumferential wall 6.3 of the retraction member 6 and the transversal wall 7.2 of the insertion member 7 define an insertion cavity 10. The insertion member 7 may comprise a seal member 11.1 for gas-tightly sealing against the circumferential wall 6.3 of the retraction member 6. A flow channel 12 in the form of a needle having a sharp proximal tip is arranged in the transversal wall 6.2 of the retraction member 6 adapted to pierce the distal wall 9.1 of the gas tank 9 to connect the gas tank 9 with the insertion cavity 10.

The transversal wall 7.2 and the circumferential wall 7.3 of the insertion member 7 and the stopper 5 of the drug cartridge 3 define a dispense cavity 13. The proximal collar 3.1 is gas-tightly fitted within the insertion member 7, e.g. by a seal.

A flow limiter 14 is arranged in the transversal wall 7.2 of the insertion member 7 to limit a gas flow between the insertion cavity 10 and the dispense cavity 13. A flexible membrane 15 is arranged in the circumferential wall 7.3 of the insertion member 7. The retraction release member 8 comprises a radially inwardly directed protrusion 8.2 adapted to be engaged by the flexible membrane 15 when the flexible membrane 15 is outwardly deformed if the pressure within the dispense cavity 13 exceeds a predetermined value. The retraction release member 8 can thus be thus outwardly deflected such that the hook 8.1 disengages from the recess 6.1 in the retraction member 6.

The retraction member 6 is sealed against an inner surface of the housing 2 by two axially spaced seal members 11.2, 11.3, the more proximally arranged seal member 11.2 arranged on the retraction member 6 and the more distally arranged seal member 11.3 arranged on the housing 2. An outer diameter of the retraction member 6 is smaller than an inner circumference of the housing 2 such that a retraction cavity 16 is defined by the retraction member 6, the housing 2 and the seal members 11.2, 11.3. In an exemplary embodiment, the seal member 11.2 may be arranged on a circumferential rib 6.4 on the retraction member 6 and/or the seal member 11.3 may be arranged on a circumferential rib 2.1 within the housing 2 to radially space the retraction member 6 from the housing 2.

A bleed hole 17 is arranged in the circumferential wall 6.3 of the retraction member 6 to connect the insertion cavity 10 with the retraction cavity 16.

Figure 2:
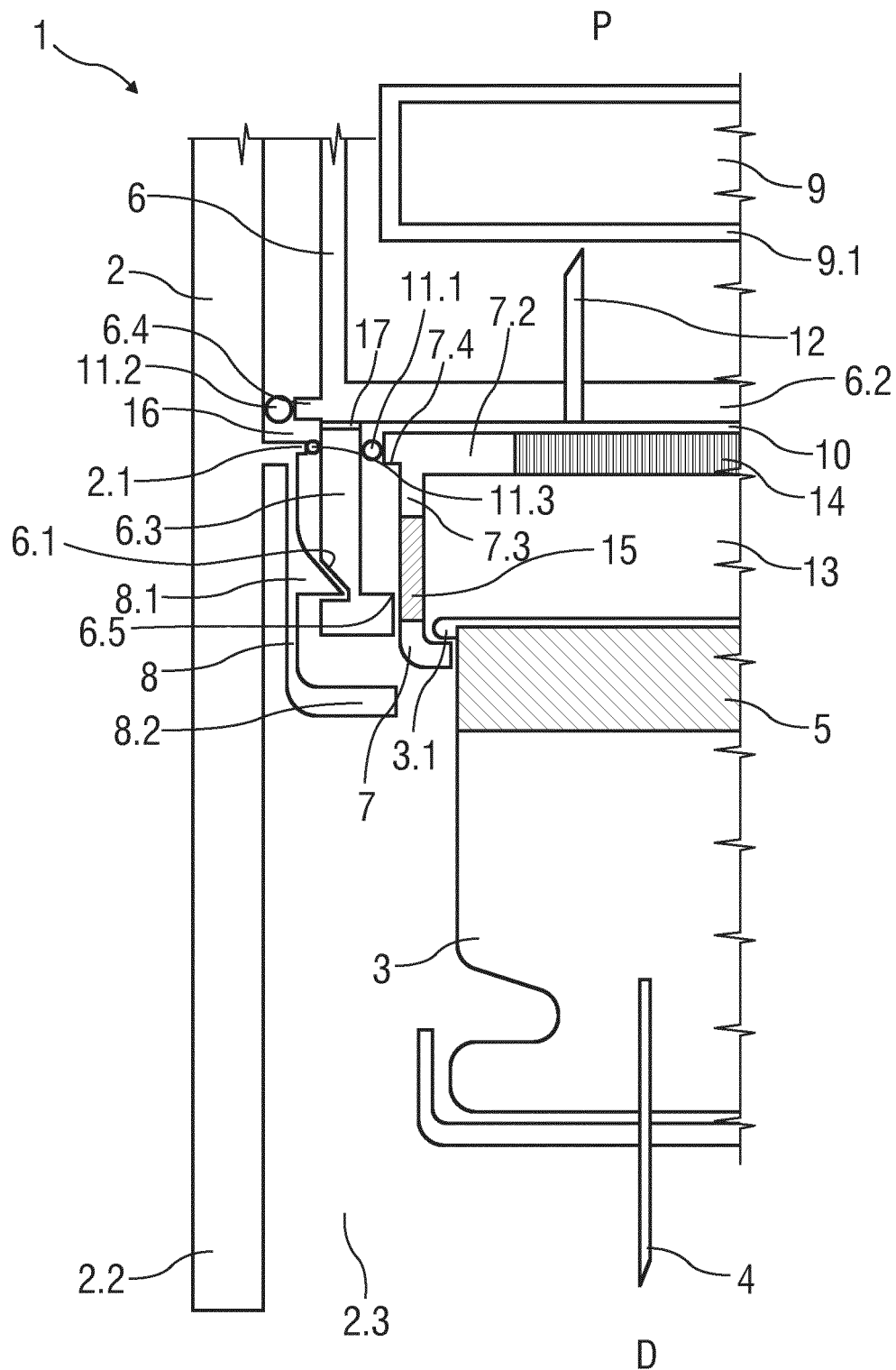
FIG. 2 is a schematic detail view of the drug delivery device prior to use.

FIG. 2 is a schematic detail view of the drug delivery device 1 in a state prior to use as it would be presented to a user. The retraction member 6 is in a distal position coupled by the retraction release member 8 with the housing 2. The gas tank 9 is in a proximal position such that the flow channel 12 is spaced from the distal wall 9.1 of the gas tank 9. The insertion member 7 is in a proximal position within the retraction member 6. The drug cartridge 3 is thus also in a proximal position within the housing 2 such that the injection needle 4 is hidden within the housing 2.

Figure 3:
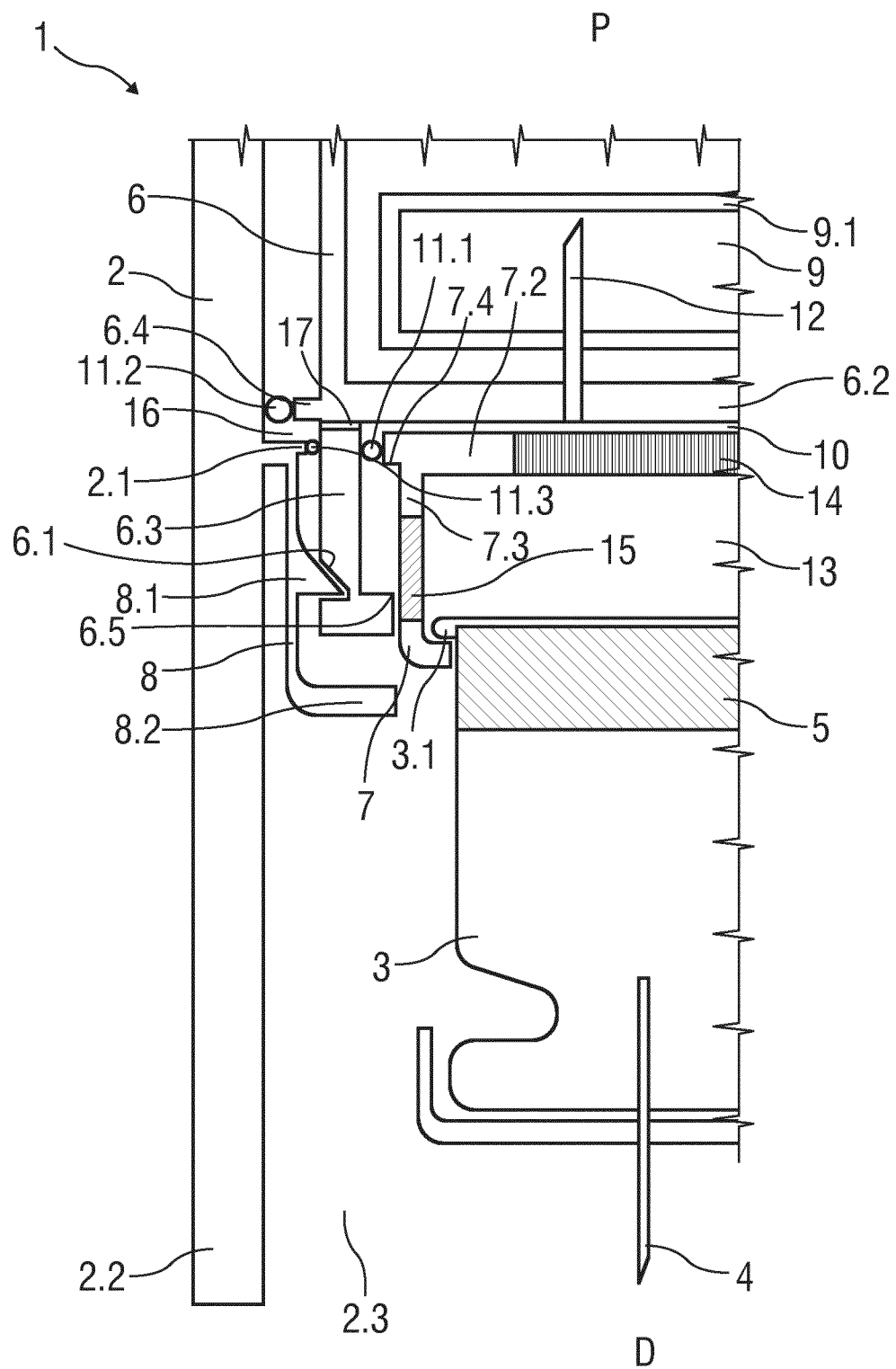
FIG. 3 is a schematic detail view of the drug delivery device during pre-activation.

FIG. 3 is a schematic detail view of the drug delivery device 1 during pre-activation. The gas tank 9 has been moved in the distal direction D by a user towards the retraction member 6. The flow channel 12 thus pierces the distal wall 9.1 of the gas tank 9 such that the pressurized gas flows from the gas tank 9 through the flow channel 12 into the insertion cavity 10. The gas flows further through the bleed hole 17 into the retraction cavity 16.

Figure 4:
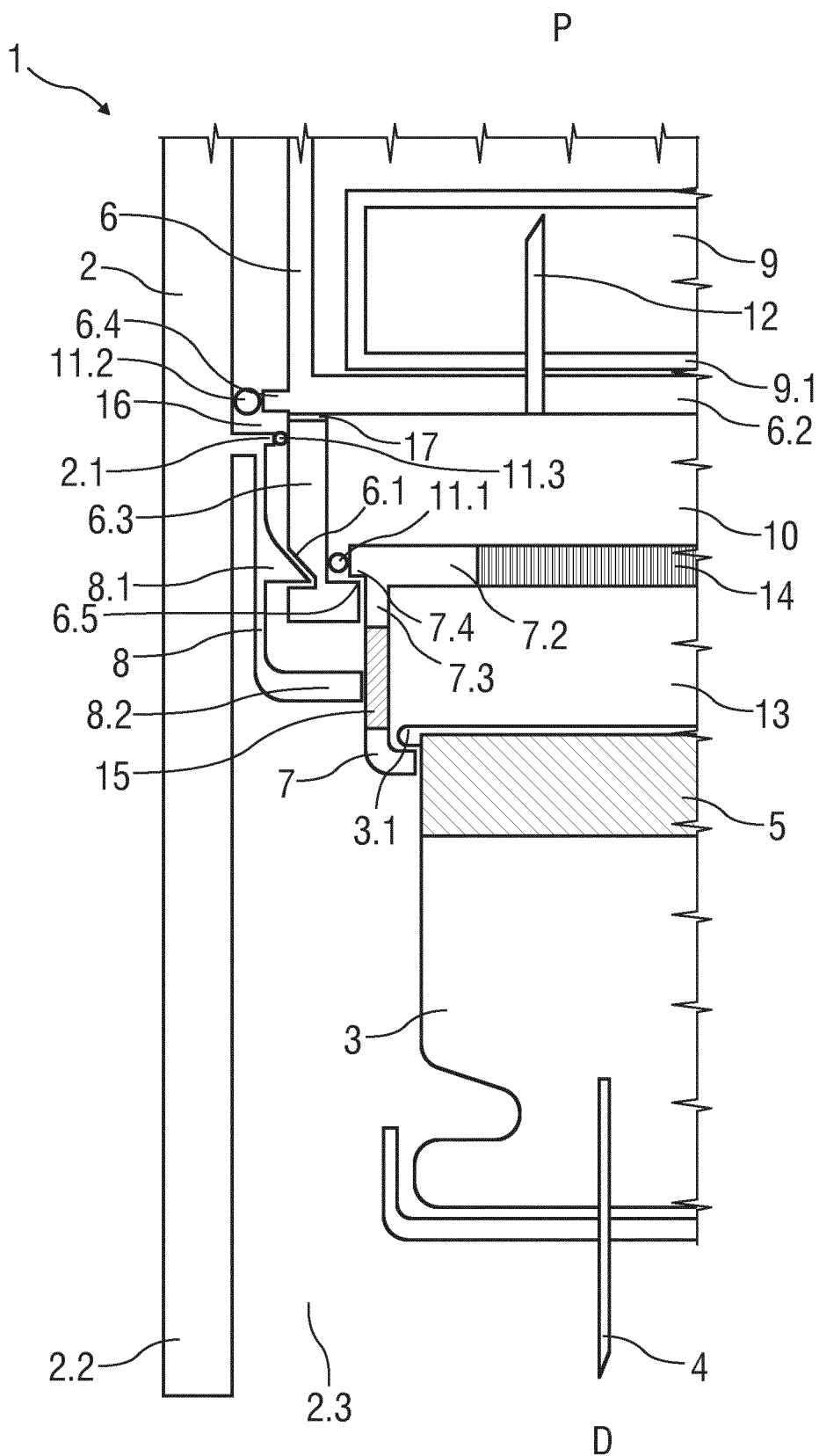
FIG. 4 is a schematic detail view of the drug delivery device during needle insertion.

FIG. 4 is a schematic detail view of the drug delivery device 1 during needle insertion. Due to the increased pressure in the insertion cavity 10, the insertion member 7 and the drug cartridge 3 with the needle 4 are moved in the distal direction D relative to the retraction member 6 and the housing 2 such that the injection needle 4 protrudes beyond a distal end 2.2 of the housing 2 through an opening 2.3 and may thus be inserted into an injection site, e.g. a patient's skin. The pressure also increases in the retraction cavity 16 but the retraction member 6 cannot move in the proximal direction P as it is coupled to the housing 2 by the hook 8.1 of the retraction release member 8 engaging the recess 6.1.

Figure 5:
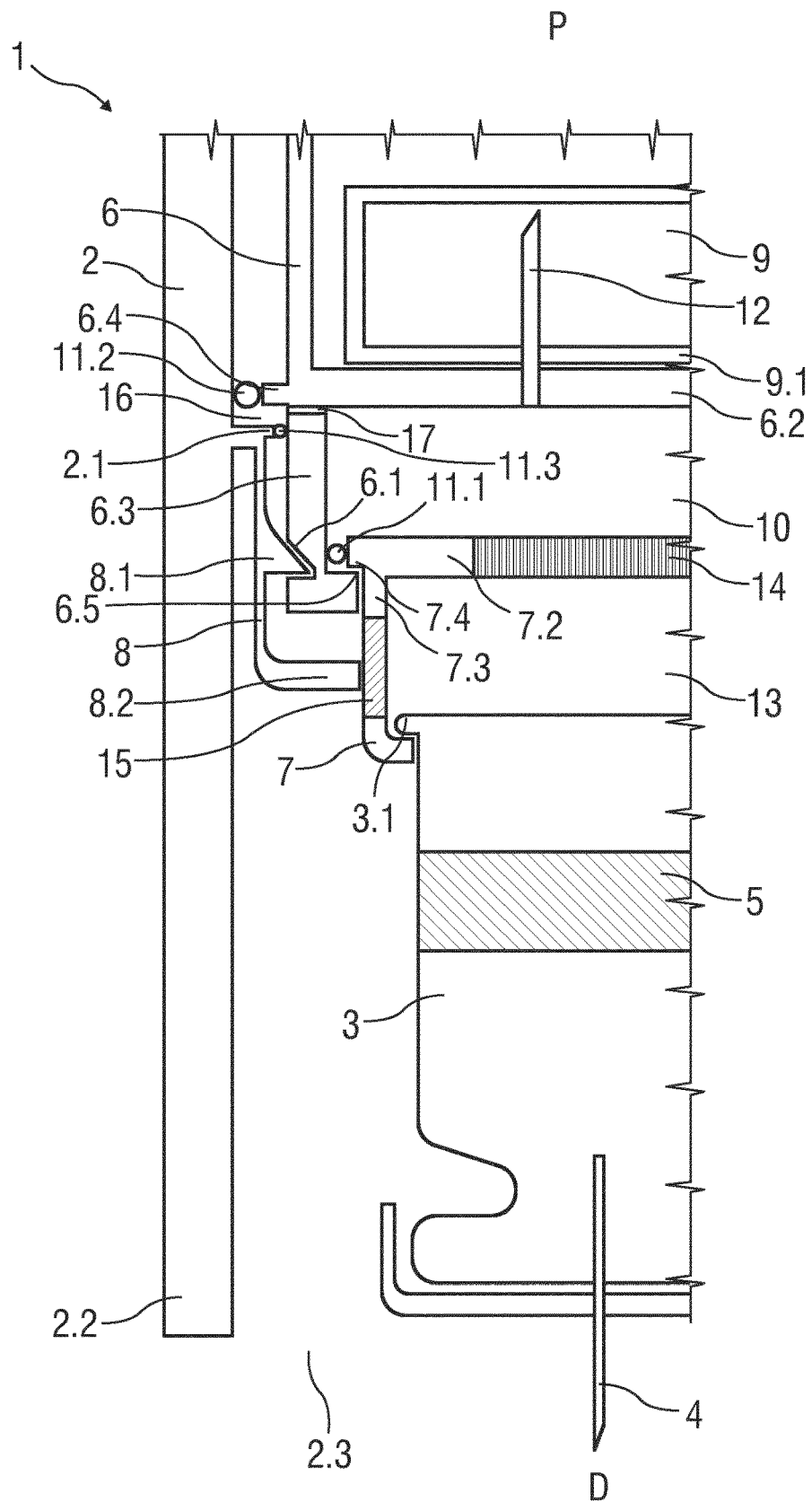
FIG. 5 is a schematic detail view of the drug delivery device during drug delivery.

FIG. 5 is a schematic detail view of the drug delivery device 1 during drug delivery. During needle insertion, the volume of the insertion cavity 10 has increased due to the insertion member 7 moving in the distal direction D within the retraction member 6. This movement ends as respective stops 6.5, 7.4 on the retraction member 6 and the insertion member 7 abut each other. As the volume does not increase further, continued flow of pressurized gas results in an increase of the pressure within the insertion cavity 10 so that pressurized gas flows through the flow limiter 14 from the insertion cavity 10 into the dispense cavity 13. Due to the increase of pressure in the dispense cavity 13, the stopper 5 is moved within the drug cartridge 3 in the distal direction D, displacing the drug from the drug cartridge 3 through the injection needle 4 into the injection site.

Figure 6:
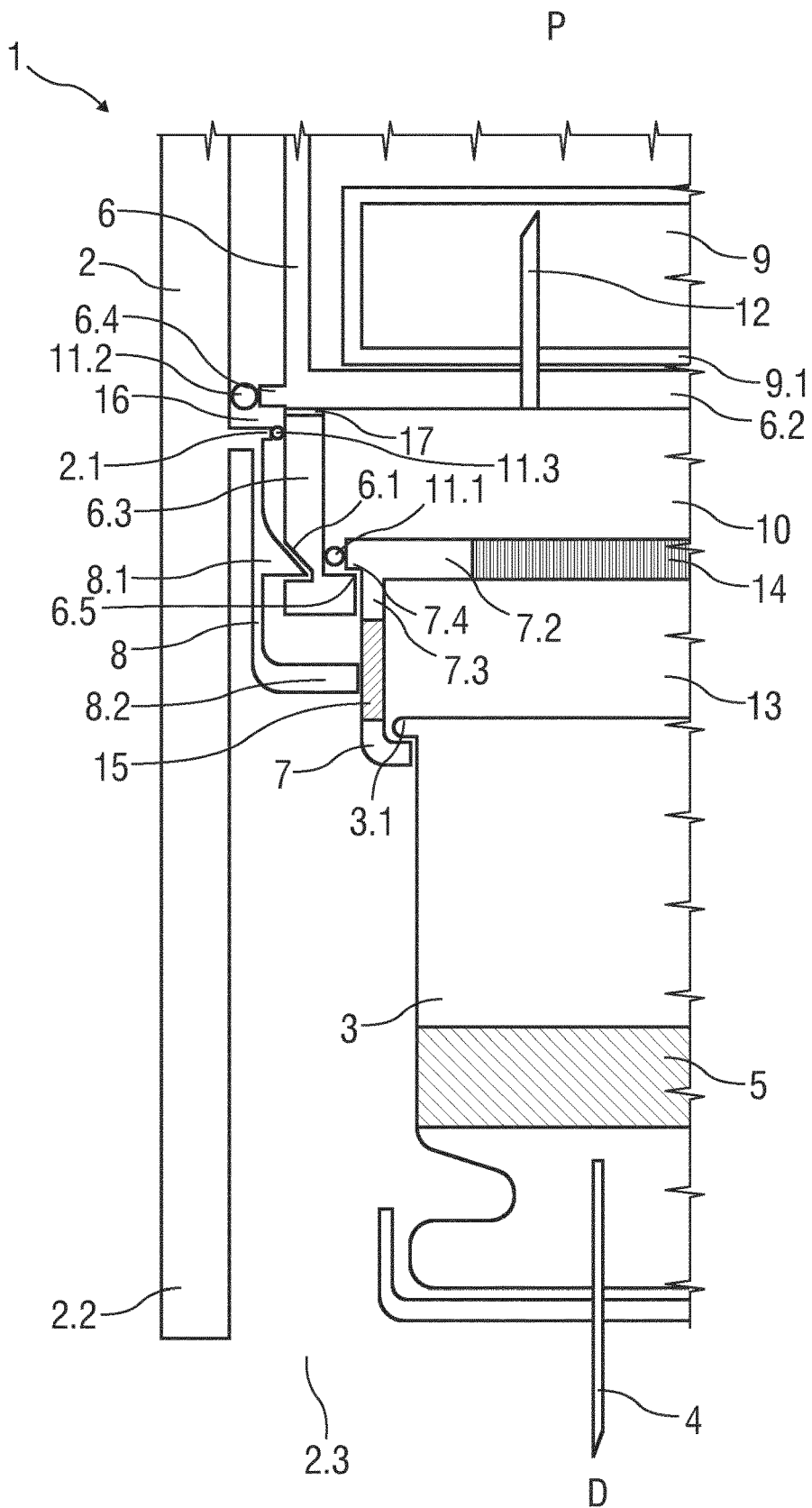
FIG. 6 is a schematic detail view of the drug delivery device at the end of drug delivery.

FIG. 6 is a schematic detail view of the drug delivery device 1 at the end of drug delivery. The movement of the stopper 5 has continued until the stopper 5 has bottomed out within the drug cartridge 3.

Figure 7:
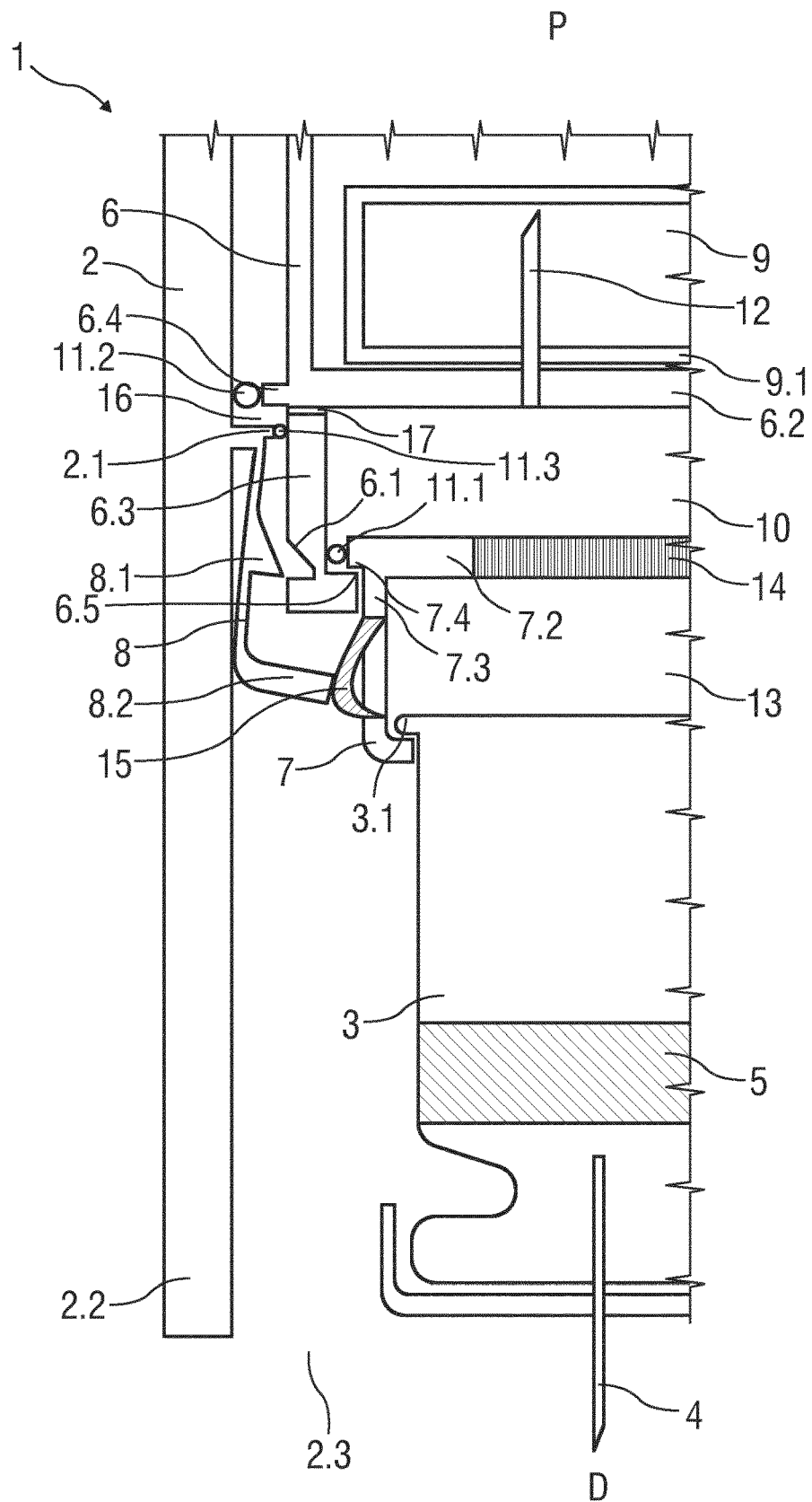
FIG. 7 is a schematic detail view of the drug delivery device during needle retraction.

FIG. 7 is a schematic detail view of the drug delivery device 1 during needle retraction. During drug dispense, the volume of the dispense cavity 13 has increased due to the stopper 5 moving in the distal direction D within the drug cartridge 3. As this movement ends when the stopper 5 bottoms out in the drug cartridge 3, the volume does not increase further so continued flow of pressurized gas into the dispense cavity 13 results in an increase of the pressure within the dispense cavity 13 so that the flexible membrane 15 is deformed in an outward direction pushing on the protrusion 8.2 of the retraction release member 8. The retraction release member 8 is thus outwardly deflected such that the hook 8.1 disengages from the recess 6.1 in the retraction member 6. The already increased pressure in the retraction cavity 16 results in movement of the retraction member 6 in the proximal direction P, taking along the insertion member 7, the drug cartridge 3 and the injection needle 4.

Figure 8:
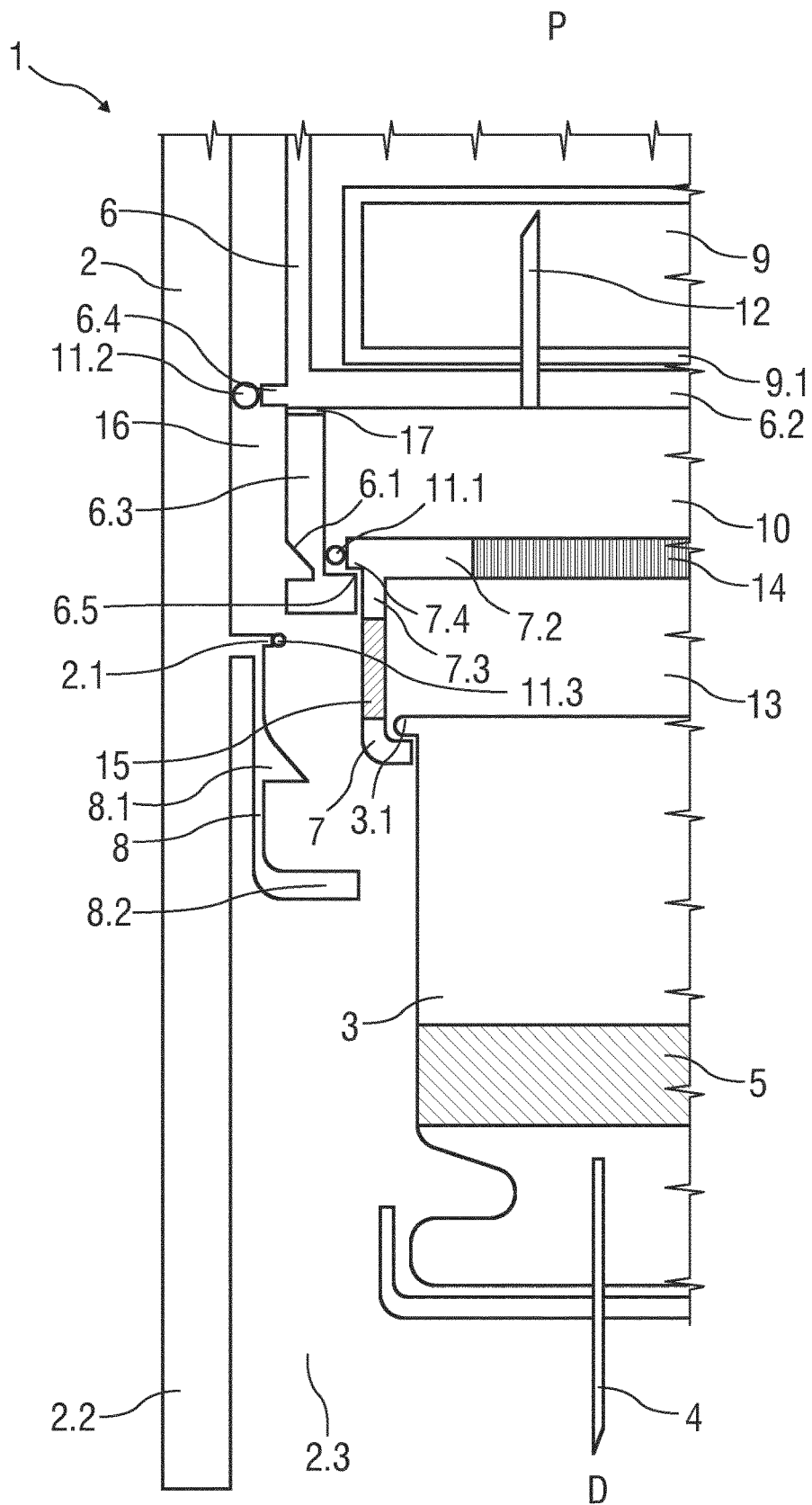
FIG. 8 is a schematic detail view of the drug delivery device at the end of needle retraction.

FIG. 8 is a schematic detail view of the drug delivery device 1 at the end of needle retraction. Due to the movement of the retraction member 6 in the proximal direction P, taking along the insertion member 7, the drug cartridge 3 and the injection needle 4, the injection needle 4 is retracted into the housing 2. As a distal end 6.6 of the retraction member 6 moves proximally beyond the seal member 11.2 on the housing 2, the retraction cavity 16 becomes untight and the pressurized gas can thus escape from the retraction cavity 16. This generates an audible feedback informing the user that the injection cycle has ended.

Figure 9:
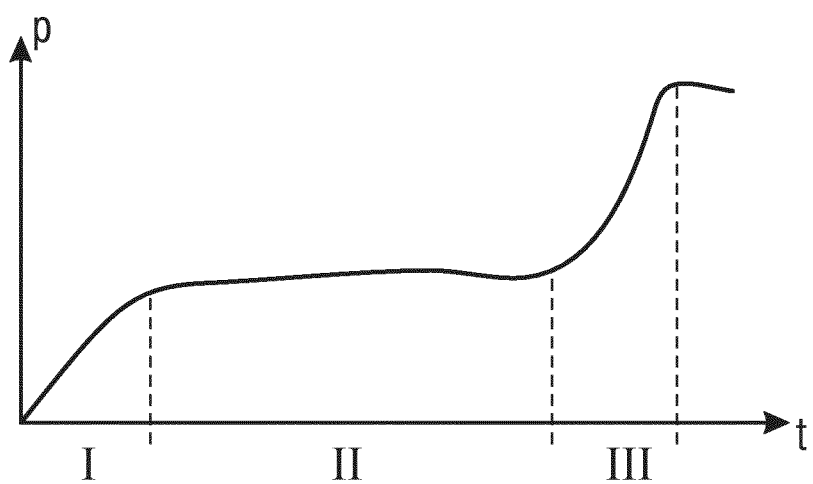
FIG. 9 is a diagram showing a pressure characteristic vs. time.

FIG. 9 is a diagram showing a pressure p in the dispense cavity 13 vs. time t. At the beginning of a time period I, the gas tank 9 is pierced by the flow channel 12 and the pressure p begins to build up in the dispense cavity 13. During time period I, the drug delivery device 1 runs through the states as shown in FIGS. 3 and 4. At the end of time period I the pressure p is high enough to overcome a break-loose force of the stopper 5 so the stopper 5 starts to move in the distal direction D as shown in FIGS. 5 and 6 in time period II. During time period II, the pressure p in the dispense cavity 13 remains substantially on the same level. At the end of time period II, the stopper 5 has bottomed out in the drug cartridge 3 as shown in FIG. 6 and the pressure p builds further up in the dispense cavity 13 in time period III. At the end of time period III, the flexible membrane 15 operates the retraction release member 8 as shown in FIG. 7 so the volume of the retraction cavity 16 increases so the pressure p in the dispense cavity 13 substantially remains on its level. As the drug delivery device 1 arrives in the state as shown in FIG. 8, the retraction cavity 16 becomes untight so the pressure p would decay down to its initial level.

The drug delivery device 1 of the present disclosure allows for an injection cycle with an automatic sequence of operation. The pressurized gas allows for a particularly high dispensing force suitable for injecting high-viscosity drugs. The acceleration and impact on the drug cartridge 3 is smooth as can be seen in FIG. 9 so that the risk of damaging the drug cartridge 3 is reduced. The drug delivery device 1 provides post-injection needle safety by automatic needle retraction.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 drug delivery device
2 housing
2.1 circumferential rib
2.2 distal end
2.3 opening
3 drug cartridge
3.1 proximal collar
4 injection needle
5 stopper
6 retraction member
6.1 recess
6.2 transversal wall
6.3 circumferential wall
6.4 circumferential rib
6.5 stop
6.6 distal end
7 insertion member
7.2 transversal wall
7.3 circumferential wall
7.4 stop
8 retraction release member
8.1 hook
8.2 protrusion
9 gas tank
9.1 distal wall
10 insertion cavity
11.1 seal member
11.2 seal member
11.3 seal member
12 flow channel
13 dispense cavity
14 flow limiter
15 flexible membrane
16 retraction cavity
17 bleed hole
D distal direction
P proximal direction

The invention claimed is:

1. A drug delivery device, comprising:
a housing adapted to receive a drug cartridge with an injection needle and a stopper, wherein the drug cartridge is axially movable within the housing so as to operatively cover the injection needle within the housing or advance the injection needle beyond a distal end of the housing,
a gas tank containing a pressurized gas arranged within the housing, the gas tank operatively connectable with an insertion cavity for moving the drug cartridge in a distal direction, a dispense cavity for moving the stopper in the distal direction and a retraction cavity for moving the drug cartridge in a proximal direction,
a retraction member slideably arranged within the housing,
a retraction release member fixed to the housing and adapted to restrict movement of the retraction member relative to the housing in the proximal direction,
a flexible membrane between the dispense cavity or the insertion cavity and the retraction release member, the flexible membrane being adapted to operate the retraction release member when the flexible membrane is deformed by a pressure within the dispense cavity or the insertion cavity exceeding a predetermined value allowing movement of the drug cartridge relative to the housing in the proximal direction.

2. The drug delivery device according to claim 1, comprising:
an insertion member slidably arranged within the retraction member and adapted to hold the drug cartridge such that the insertion member and the drug cartridge cannot move relative to each other in an axial direction,
wherein the retraction release member is fixed to the housing and adapted to engage the retraction member for restricting movement of the retraction member relative to the housing in the proximal direction.

3. The drug delivery device according to claim 2, wherein the insertion cavity is defined within the retraction member and operatively connectable to the gas tank by a flow channel, the insertion cavity adapted to move the insertion member in the distal direction when subjected to pressure.

4. The drug delivery device according to claim 3, wherein the dispense cavity is defined within the insertion member and adapted to be distally limited by the stopper so as to displace the stopper in the distal direction when subjected to pressure, wherein the dispense cavity is separated from the insertion cavity by a flow limiter in the insertion member.

5. The drug delivery device according to claim 2, wherein the flexible membrane is arranged in the insertion member and adapted to disengage the retraction release member from the retraction member if the flexible membrane is deformed by the pressure within the dispense cavity exceeding the predetermined value.

6. The drug delivery device according to claim 2, wherein the retraction cavity is defined between the housing and the retraction member and adapted to move the retraction member in the proximal direction when subjected to pressure, wherein the retraction cavity is connected with the insertion cavity by a bleed hole.

7. The drug delivery device according to claim 2, wherein the insertion member is adapted to engage a proximal collar on the drug cartridge.

8. The drug delivery device according to claim 2, wherein the gas tank is slidable in an axial direction and comprises a distal wall arranged as or comprising a piercable membrane, wherein a flow channel in the form of a needle having a sharp proximal tip is arranged in the retraction member adapted to pierce the distal wall of the gas tank to connect the gas tank with the insertion cavity.

9. The drug delivery device according to claim 2, wherein the retraction member comprises a transversal wall and a circumferential wall and/or wherein the insertion member comprises a transversal wall and a circumferential wall.

10. The drug delivery device according to claim 9, wherein the insertion member comprises a seal member for gas-tightly sealing against the circumferential wall of the retraction member.

11. The drug delivery device according to claim 2, wherein the retraction release member comprises a hook for engaging a recess in the retraction member.

12. The drug delivery device according to claim 2, wherein the retraction member is sealed against an inner surface of the housing by two axially spaced seal members, a more proximally arranged seal member arranged on the retraction member and a more distally arranged seal member arranged on the housing thus sealing the retraction cavity.

13. The drug delivery device according to claim 12, wherein an outer diameter of the retraction member is smaller than an inner circumference of the housing.

14. The drug delivery device according to claim 13, wherein the more proximally spaced seal member is arranged on a circumferential rib on the retraction member and/or wherein the more distally spaced seal member is arranged on a circumferential rib within the housing to radially space the retraction member from the housing.

15. The drug delivery device according to claim 1, wherein the retraction release member comprises a radially inwardly directed protrusion adapted to be engaged by the flexible membrane.

16. The drug delivery device according to claim 1, wherein the flexible membrane is adapted to disengage the retraction release member when the flexible membrane is deformed by the pressure within the dispense cavity exceeding the predetermined value.

17. The drug delivery device according to claim 1, wherein the gas tank is slidable in an axial direction and comprises a distal wall arranged as or comprising a piercable membrane, wherein a flow channel in the form of a needle having a sharp proximal tip is adapted to pierce the distal wall of the gas tank.

18. The drug delivery device according to claim 1, wherein the dispense cavity is adapted to be distally limited by the stopper so as to displace the stopper in the distal direction when subjected to pressure.

19. The drug delivery device according to claim 1, wherein the retraction release member comprises a hook.

20. The drug delivery device according to claim 1, wherein the retraction cavity is connected with the insertion cavity by a bleed hole.

* * * * *